United States Patent [19]

Mälson

[11] Patent Number: 4,963,666

[45] Date of Patent: Oct. 16, 1990

[54] MATERIAL OF POLYSACCHARIDES CONTAINING CARBOXYL GROUPS, AND A PROCESS FOR PRODUCING SUCH POLYSACCHARIDES

[75] Inventor: Tomas Mälson, Uppsala, Sweden

[73] Assignee: Pharmacia AB, Uppsala, Sweden

[21] Appl. No.: 145,780

[22] PCT Filed: Jun. 9, 1987

[86] PCT No.: PCT/SE87/00272

§ 371 Date: Jan. 27, 1988

§ 102(e) Date: Jan. 27, 1988

[87] PCT Pub. No.: WO87/07898

PCT Pub. Date: Dec. 30, 1987

[30] Foreign Application Priority Data

Jun. 18, 1986 [SE] Sweden .............................. 8602705-9

[51] Int. Cl.$^5$ .................... C08B 37/00; C08B 37/08
[52] U.S. Cl. ...................... 536/55.1; 536/2; 536/21; 536/47; 536/63; 536/55; 536/80; 536/98; 536/106; 536/112; 527/300; 527/301
[58] Field of Search .................. 536/55.1, 2, 21, 47, 536/55, 63, 80, 98, 106, 112; 514/54; 527/300, 301

[56] References Cited

U.S. PATENT DOCUMENTS

| | | | |
|---|---|---|---|
| 3,042,667 | 7/1962 | Flodin et al. | 536/112 |
| 3,420,788 | 1/1969 | Solms | 527/300 |
| 4,002,173 | 1/1977 | Manning et al. | 536/112 |
| 4,076,930 | 2/1978 | Ellingboe et al. | 536/112 |
| 4,370,476 | 1/1983 | Usher et al. | 536/112 |
| 4,535,152 | 8/1985 | Szejtli et al. | 527/300 |
| 4,713,448 | 12/1987 | Balazs et al. | 536/55.1 |
| 4,716,224 | 12/1987 | Sakurai et al. | 536/55.1 |
| 4,794,177 | 12/1988 | Peska et al. | 536/112 |
| 4,814,437 | 3/1989 | deBelder et al. | 536/112 |

FOREIGN PATENT DOCUMENTS 161887 11/1985 European Pat. Off. .

Primary Examiner—Ronald W. Griffin
Attorney, Agent, or Firm—Fred Philpitt

[57] ABSTRACT

Method of crosslinking carboxyl-containing polysaccharides in that the polysaccharide is at first activated with a bi- or polyfunctional reagent, and then after removal of any potential excess of activating reagent the crosslinking is performed during drying. The invention also comprises a material produced according to this method.

7 Claims, No Drawings

MATERIAL OF POLYSACCHARIDES CONTAINING CARBOXYL GROUPS, AND A PROCESS FOR PRODUCING SUCH POLYSACCHARIDES

The present invention relates to a chemically crosslinked material of polysaccharides which contain carboxyl groups. The process for producing this material provides a possibility of varying, within a wide range, the degradability of this material under physiological conditions.

Insoluble polymeric materials of varying degradability in physiological environments are useful for a broad spectrum of medical applications; for instance they may be employed for surgical implants, e.g. in order to prevent tissue adhesion, or for wound dressing bandages or for slow release depots of drugs.

A method commonly employed for producing insoluble polymeric materials involves covalent crosslinking of soluble polymers with bifunctional or polyfunctional reagents. Crosslinking of polysaccharides is often performed by reacting the hydroxyl groups of the polysaccharides in an alkaline aqueous solution with bi- or polyfunctional epoxides to thus bind the polysaccharide chains to one another via ether bonds, with concomitant formation of a gel. The ether bonds however are not degradable at a physiological pH; such a gel material therefore may prove to be very stable to degradation. An example of such an ether-bonded gel is given in Swedish patent application 8403090-7 which describes the use of a non-degradable crosslinked gel of hyaluronic acid as a vitreous humor substitute.

A process for producing degradable polysaccharide gels is described in Swedish patent application 8403817-3 according to which carboxyl groups of the polysaccharides are crosslinked with di- or polyfunctional epoxides by means of acid catalysis, whereby an insoluble gel is formed. In this case the bonds produced are ester bonds which in contrast to ether bonds are degradable in physiological environments; degradation times of such gels will typically be about 2 to 3 days.

The aforesaid gels, i.e. those produced under acid catalysis conditions and those produced under alkaline catalysis conditions, are manufactured and used in a swollen state; but the Swedish patent application SE 8501022-1 describes also methods for drying hyaluronic acid gels to thus obtain products of improved mechanical stability.

Dry films of hyaluronic acid are also known from the German patent application DE 3434082 which contains examples according to which hyaluronic acid and crosslinking agent are dried to form an insoluble product.

Although the method of SE 840317-3 allows for some variation in the degradation time of the resultant gel it will nevertheless be desirable to have a possibility of varying the degradation time within a wider range, and in a controllable manner.

We have now surprisingly found a novel method for producing gels of crosslinked polysaccharides by which it becomes possible inter alia to combine the aforesaid methods for acid- and base-catalyzed crosslinking so as to produce novel gel materials of controllable degradability. The present novel process moreover enables the crosslinking reaction to be carried out also with a low content of the activating reagent required for the crosslinking; this means that only very small amounts of residual reagent or degradation products thereof can potentially be released from the gel.

Such leakage from the gel may occur if the gel is used for a long period of time or in the course of controlled degradation, and is a factor to be taken into consideration in accordance with the particular environmental conditions in the practical use of the gel.

The principle of the manufacturing process is as follows: The polysaccharide containing carboxyl groups is at first reacted with a bi- or polyfunctional epoxide. This reaction may be performed in an alkaline, acidic or neutral medium and consists in a so-called epoxy-activation of the polysaccharide. The conditions chosen are such that no gel formation takes place in this stage; instead, the polysaccharide in this stage is still to be soluble. Next follows removal of excess epoxide i.e. of reagent that has not bound to the polysaccharide. Thereafter the polysaccharide is dried at a desired pH. In the course of the drying process the polysaccharide molecules which have been epoxy-activated in the preceding step will move into closer proximity to each other and will become crosslinked. It is this drying procedure that forms the crosslinking step, thus constituting a fundamental difference from conventional crosslinking in solution.

The process thus differs to an essential degree also from that described in the aforesaid patent application DE 3434082 according to which crosslinking agent and hyaluronic acid are mixed and then dried to form a dry film; this process will not permit such regulation of subsequent degradation as is characteristic of the process of the present invention.

Examples of carboxyl-containing polysaccharides that may be employed in the process of the invention are naturally carboxyl-containing polysaccharides such as e.g. hyaluronic acid, pectin, xanthan, alginic acid, and anionic derivatives of neutral polysaccharides such as e.g. carboxymethyl cellulose, carboxymethyl dextran or carboxymethyl starch. The process is particularly useful for producing water-swellable films of hyaluronic acid.

Epoxy-type activating reagents employed are bi- or polyfunctional epoxides, e.g. lower aliphatic epoxides or their corresponding epihalohydrins. Among such reagents that are well known to persons skilled in the art may be mentioned e.g. 1,4-butanediol diglycidyl ether, 1,2-ethanediol diglycidyl ether, epoxy-substituted pentaerythritol (e.g. SHELL 162) and epihalohydrins thereof.

Conditions in which the initial epoxy-activation takes place may be varied within a wide range and are chosen according to the properties desired in the final product. An important point is that gel formation has to be avoided in this initial step. This means, in particular, that the concentration of polysaccharide must not be too high. In many systems this in turn means that the concentration should not exceed about 15% (w/w); preferably it should be within the range of 0,1-10%.

As has been mentioned above ester bonds are obtained under acidic reaction conditions. Where it is desired to introduce this type of degradable bonds in the first step a pH is chosen within the range of from 2 to 6, preferably 3-5. By contrast, stable ether bonds are obtained if the activation is carried out at a pH >8, preferably in the range of pH 10-13. At a neutral pH (pH 6-8) a mixture of the two types of bonds will be obtained.

The amount of activating reagent in the reaction mixture may also be varied within wide limits, from about 1 to 75% (by weight, based on the amount of polysaccharide), although preferably lower concentrations are chosen viz. of about 1–30% which will give a low content of substituents in the final product.

It is important to note that the amount of substituents in the final product is far less than would be expected from the ratio employed in the synthesis.

The simplest and gentlest way of proceeding implies using room temperature conditions during the reaction, but depending on the particular starting material in each case and on the desired properties of the final product it is of course also possible to choose an elevated temperature. Activation times may be varied within wide limits, e.g. from 15 min. to one 24-hour day. Preferably however the reaction will take place at room temperature and proceed for more than 1 hour, inasmuch as a longer, gentler treatment will generally provide better possibilities of obtaining reproducible products.

After the initial epoxy-activation step non-bound epoxide is removed from the reaction mixture. By doing this one will make sure that the final product is free of residual unreacted epoxy-activation reagent, this being expecially important in cases where medical uses are contemplated.

The crosslinking reaction which constitutes the final step is carried out in that after adjustment to a suitable pH (which as has been explained above implies selection of the bond type) the solution is dried so as to give a product in the desired shape. The products thus may be planar films or any other shape as desired and conforming to the shape of the containers or molds employed. The solution may be dried at room temperature or at a somewhat elevated temperature; in the case of hyaluronic acid the temperature will suitably be below 70° C. Other drying methods too may be employed, it being possible thereby to bestow special properties on the product. For instance, freeze drying or spray drying may produce porous or pulverulent materials.

An example of a product according to the invention is the material obtained if the initial activation is carried out with a bi- or polyfunctional epoxide in an alkaline medium and the final crosslinking is carried out in an acidic medium after removal of non-bound reagent. Alternatively, the activation may be performed in an acidic medium and the final crosslinking in an alkaline medium; the thus resultant product is another example of a product according to the invention. It will be appreciated that in both cases the final product will contain both ester bonds and ether bonds —thus resulting in a controllably degradable product.

When only alkaline catalysis is employed in the manufacturing procedure then stable products will be obtained which are not degradable. Acid catalysis employed in both steps will give degradable products but no possibility to regulate such degradation despite the fact that of course the content of crosslinking agent can be varied.

Removal of excess crosslinking agent may be carried out for example with the aid of a semipermeable membrane, e.g. by ultrafiltration or dialysis against a medium in which the reagent residues are soluble. For example, the polysaccharide may be enclosed within a container of such a membrane which is rinsed with distilled water.

To carry out the adjustment to a desired pH one will preferably choose volatile components in the second crosslinking reaction step. Ammonia is a good choice for achieving an alkaline environment for the crosslinking reaction whereas acetic acid is an example of a good choice for producing an acidic medium. In cases where the polysaccharide has been dialysed against distilled water, a sufficiently strong acidic medium is obtained due to the weak acidity provided by the content of dissolved carbon dioxide in such water.

The substrate on which the solution is dried should have suitable hydrophilic/lipophilic characteristics. If materials of a very pronounced hydrophilic nature are employed, as e.g. glass, the film obtained upon drying will stick thereto. The film can however be released from the surface by wetting. If materials of a highly lipophilic character are employed like Teflon ® then the solution will form droplets during the drying procedure because of the low degree of wetting. We have found that particularly suitable substrates are materials having properties similar to those of polystyrene. Furthermore it is important that the solution before drying is liberated from non-volatile components, because these would contribute to opaqueness and cracking tendencies of the film.

In degradable materials according to the invention the content of substituents may vary from less than 0,1% by weight (substituents/polysaccharide) up to about 10%. The lower value is within the lower part of the range permitted by the measuring method employed (NMR). As expressed in mole-% (moles of substituents/moles of disaccharide repeating unit in the polysaccharide) the said values correspond to 0,002–0,14 if the activation reagent is butanediol diglycidyl ether (BDDE) and the polysaccharide is hyaluronic acid.

In products of the invention the residual water content (=water content after the drying step) is less than about 10%.

Dried films produced in this manner have good mechanical properties. Their tensile strength in a dry state exceeds 5 000 N/cm$^2$. In a wet state (in physiological saline) the gels will show varying tensile strength values which however may be said to be preferably higher than 400 N/cm$^2$.

Liquid uptake capacity of crosslinked polymeric materials is a measure of the efficiency with which the crosslinking agent has been utilized for cross link formation. In the materials produced in accordance with the invention this capacity is low, in typical cases 1,5- to 5-fold (in physiological saline) or 20–70% based on solids. Already when the content of substituents is as low as some tenths of one percent films of e.g. hyaluronic acid will show such a low uptake of liquid. This should be compared with crosslinked polysaccharide gels which have been produced in solution in the conventional manner; these gels have a much higher liquid uptake even though the amount of crosslinking reagents exceeds 10%.

After activation of the polysaccharide and removal of excess reagent one or more further polysaccharides may be added within the concept of this invention before the solution is subjected to drying. In particular, if the final crosslinking step is performed in an acidic medium the last-added component(s) will be bound through ester bonds and thus be releasable as intact molecules. Also components other than polysaccharides may of course be bound into the material in this manner. Examples of these are therapeutic agents of various types where a slow release of the substance is desired. Incorporation of components can thus be achieved quite simply by means of having the components present during the drying stage or binding them into polysaccharide molecules upon activation thereof.

A number of Examples will be set forth below in order to illustrate the invention without limiting the invention in any way.

Degradation times of the gels have been measured by incubation at 37° C. in phosphate-buffered physiological saline, pH 7,3. Recourse was had to filtration for checking that all the gel had dissolved.

Water contents in the dry gels have been measured by GLC after extraction with dry dimethyl sulfoxide.

Uptake of liquid has been measured after swelling of the dried products for 20 min. in 0,9% physiological saline.

Contents of substituents have been measured by means of $^1$H NMR after acid hydrolysis in a solution of deuterated acid.

Tensile strengths have been determined on films of 0,5–1 cm width with a strain gauge at a pulling rate of 1 cm/min. Tensile strength in wet condition has been measured with the slabs swelled in 0,9% physiological saline.

EXAMPLES 1. 200 mg of sodium hyaluronate $\overline{M}w$ $3 \times 10^6$ were mixed with 6 ml of 0,5% NaOH in a plastics tube. The mixture was stirred with a glass rod until a clear homogeneous solution had been obtained. Then 2 μl of 1,4-butanediol diglycidyl ether (BDDE) were added and admixed thoroughly. The solution was subjected to shaking overnight.

The solution was dialysed against running distilled water for 24 hours in a dialysis tube (Union Carbide, regenerated cellulose, separation limit $\overline{M}w$ 12,000–14,000). After this dialysis the solution had a weakly acidic pH of about 5,5.

The solution was poured into a petri dish of polystyrene having a diameter of 5 cm. It was kept for drying in a draught-free room for 2 days at room temperature. A transparent, planar, water-insoluble film was obtained, weight 150 mg, thickness 50 μm.

The film, which had a water content of 9,4% in the dry state, was found to have a degradation time of 2,5 days. Uptake of liquid was 14,6 ml/g. Content of substituents was 0,15% (% by weight of crosslinking agent-/polysaccharide).

2. The experiment of Example 1 was repeated but with 5 μl of BDDE. This gel film had a degradation time of 5 days. Content of substituents was 0,34%. Uptake of liquid was 4,1 ml/g. Tensile strength in moistened state was 457 N/cm$^2$.

3. The experiment of Example 1 was repeated but with 10 μl of BDDE. This gel film had a degradation time of 9 days. Content of substituents was 0,76%. Uptake of liquid was 4,1 ml/g.

4. The experiment of Example 1 was repeated but with 20 μl of BDDE. This gel film had a degradation time of 16 days. Water content of the dry film was 8,7%. Content of substituents was 1,66%. Uptake of liquid was 2,9 ml/g. Tensile strength was 506 N/cm$^2$ (moistened).

5. The experiment of Example 1 was repeated but with 40 μl of BDDE. Degradation time was 27 days. Uptake of liquid was 3,0 ml/g. Content of substituents was 2,61%.

6. The experiment of Example 1 was repeated but with 80 μl of BDDE. After 6 months in the buffer, the film was still undissolved. Content of substituents was 6,06%. Uptake of liquid was 3,1 ml/g. Tensile strength (moistened) was 428 N/cm$^2$.

7. The experiment was repeated as in Example 4, but 1% NaOH was substituted for the 0,5% NaOH. Degradation was 12 days. Content of substituents was 1,2%. Uptake of liquid was 2,7 ml/g.

8. The experiment was repeated as in Example 5, but the hyaluronic acid was dissolved in 6 ml of water instead of in 6 ml of 0,5% NaOH. Degradation time was 20 days. Content of substituents was 1,42%. Uptake of liquid was 1,2 ml/g.

9. The experiment was repeated as in Example 5, but the solution after having been dialysed was freeze dried. An insoluble, porous, spongy material was obtained. Degradation time was 23 days.

10. The experiment was repeated as in Example 5, but the hyaluronic acid had an average molecular weight of 215,000. The film had a degradation time of 21 days. Content of substituents was 2,0%. Uptake of liquid was 1,5 ml/g.

11. The experiment was repeated as in Example 5, but the hyaluronic acid had an average molecular weight of 40,000. The film had a degradation time of 12 days. Content of water in the dry film was 9,5%. Content of substituents was 3,0%. Uptake of liquid was 1,0 ml/g.

12. 1,5 g of sodium hyaluronate $\overline{M}w$ $1,8 \times 10^6$ was dissolved in 75 ml of 0,5% NaOH. Then 150 μl of BDDE were added and thoroughly worked in. The solution was heated at 50° C. for 30 min., whereupon 1,6 ml of conc. acetic acid was added to thus terminate the base-catalyzed activation reaction. The solution was dialysed against distilled water for one 24-hr day; thereafter it was dried on a petri dish having a diameter of 14 cm. The film thus formed had a content of substituents amounting to 0,57%. Degradation time was 2–3 days. Uptake of liquid was 10 ml/g.

13. The experiment of Example 1 was repeated, but the crosslinking agent employed in this case was 20 μl of epoxy-substituted pentaery-thritol (SHELL 162). Water content in the dry film was 8,4%. Degradation time was 42 days. Uptake of liquid was 1,6 ml/g.

14. The experiment of Example 1 was repeated, but the crosslinking agent employed in this case was 10 μl of epichlorohydrin. Degradation time was 13 days. Uptake of liquid was 2,5 ml/g.

15. 200 mg of carboxymethyl cellulose (FLUKA CMC Na salt) were dissolved in 3 ml of 0,5% NaOH, whereupon 40 μl of BDDE were added. Reaction, dialysis and film formation were carried out as in Example 1. Water content in the dry product was 6,3%. Degradation time was 43 days. Uptake of liquid was 1,6 ml/g.

16. 200 ml of carboxymethyl dextran ($\overline{M}w$ $2 \times 10^6$ D.S. 0,24) were dissolved in 3 ml of 0,5% NaOH. Reaction, dialysis and film formation were carried out as in Example 1. Degradation time was 30 days. Uptake of liquid was 12,7 ml/g.

17. 200 mg of Xanthan Gum were dissolved in 6 ml of 0,5% NaOH; 5 μl of BDDE was added. Reaction, film formation and dialysis were carried out as in Example 1. Degradation time was 24 days. Uptake of liquid was 9,5 ml/g.

18. 200 mg of sodium hyaluronate were dissolved in 5 ml of 0,5% NaOH; 10 μl of BDDE were added. The reaction was allowed to proceed for one hour at room temperature, whereupon 0,2 ml of conc. acetic acid was added and the solution was dialysed overnight and dried to form a film. Degradation time was 20–24 hours. Content of substituents was <0,1%.

19. A hyaluronic acid film was prepared in the same manner as in the foregoing example, but 2 mg of vitamin A acid were added to the alkaline hyaluronate solution. When the acetic acid is added, the alkali-soluble vitamin precipitates in the form of small crystals; in the course of the drying procedure these crystals disperse evenly in the film that is being formed. Vitamin release from the film was measured. A piece of the film weighing 6 mg (vitamin A acid content 0,06 mg) was treated in 10 ml of buffer, with an addition of 1 drop of wetting agent (Polysorb 80). Absorbance measurement at the absorbance maximum of the vitamin, 351 nm, showed continuous release of 90% of the vitamin during one 24-hr day.

| Time | 0 | 20 min | 4 hrs | 20 hrs | 28 hrs | 4 days | 6 days |
|---|---|---|---|---|---|---|---|
| Absorbance 351 nm | 0,07 | 0,08 | 0,22 | 0,77 | 0,82 | 0,85 | 0,79 |

The absorbance value of 0,82 corresponds to 0,0054 mg of vitamin A acid per ml of solution, based on a molar absorbance index of vitamin A acid amounting to 45,000 mole $\cdot$ cm$^{-1}$ lit$^{-1}$.

20. 200 mg of hyaluronic acid ($\overline{M}w$ $3 \times 10^6$) were dissolved in 6 ml of water. First 25 μl of conc. acetic acid and then 25 μl of BDDE were added. The reaction was allowed to proceed overnight. Dialysis and film formation were carried out as in Example 1. Degradation time was 7 days. Content of substituents was 0,60%. Uptake of liquid was 2,4 ml/g.

21. The experiment of Example 20 was repeated but with 50 μl of acetic acid and 50 μl of BDDE. Degradation time was 7 days. Content of substituents was 1,6%. Uptake of liquid was 2,3 ml/g.

22. The experiment of Example 20 was repeated but with 100 μl of acetic acid and 100 μl of BDDE. Degradation time was 7 days. Content of substituents was 3,1%. Uptake of liquid was 3,2 ml/g.

23. The experiment of Example 20 was repeated but with 200 μl of acetic acid and 200 μl of BDDE. Degradation time was 7 days. Content of substituents was 7,5%. Uptake of liquid was 3,0 ml/g.

24. The experiment of Example 4 was repeated, but 100 μl of ammonia (25% in water) were added to the dialysed solution prior to drying. After 6 months in the buffer, this film was still undissolved. Content of substituents was 2,7%. Uptake of liquid was 2,3 ml/g.

25. The experiment of Example 20 was repeated, but 100 μl of ammonia (25% in water) were added to the dialysed solution prior to drying. The degradation time of this product was 12 days and its uptake of liquid was 1,8 ml/g.

I claim:

1. A process for the production of crosslinked polysaccharides containing carboxyl groups which comprises
   (a) in a first step contacting a polysaccharide containing carboxyl groups with a bi- or polyfunctional epoxide so as to obtain epoxy-activation of said polysaccharide without crosslinking of said polysaccharide,
   (b) in a second step removing any epoxide that is not bound to said activated but uncrosslinked polysaccharide, and
   (c) in a third step subjecting the activated but uncrosslinked polysaccharide of step (b) to drying conditions until said epoxy-activated polysaccharides do become crosslinked.

2. A process according to claim 1 wherein the activation set forth in step (a) is carried out in an alkaline medium and the drying is performed under acidic conditions.

3. A process according to claim 1 wherein the removal of the epoxide is performed with the aid of a semipermeable membrane.

4. A process according to claim 1 wherein said polysaccharide is hyaluronic acid.

5. A process according to claim 2 wherein said polysaccharide is hyaluronic acid.

6. A process according to claim 3 wherein said polysaccharide is hyaluronic acid.

7. A process according to claim 1 wherein in step (a) most of the epoxide is bound to said saccharide by both ether and ester bonds.

* * * * *